United States Patent

Ooms et al.

Patent Number: 4,808,623
Date of Patent: Feb. 28, 1989

[54] 5-AMINO-3-HALOGENOALKYL-1-ARYL-PYRAZOLES, COMPOSITION CONTAINING THEM, AND METHOD OF USING THEM TO COMBAT INSECTS

[75] Inventors: Pieter Ooms, Krefeld; Benedikt Becker, Mettmann, both of Fed. Rep. of Germany

[73] Assignee: Bayer Aktiengesellschaft, Leverkusen, Fed. Rep. of Germany

[21] Appl. No.: 160,038

[22] Filed: Feb. 24, 1988

[30] Foreign Application Priority Data

Mar. 5, 1987 [DE] Fed. Rep. of Germany ....... 3706993

[51] Int. Cl.$^4$ .................... A01N 43/56; C07D 231/38
[52] U.S. Cl. ..................................... 514/404; 548/362
[58] Field of Search .......................... 548/362; 514/404

[56] References Cited

FOREIGN PATENT DOCUMENTS 0001019 3/1979 European Pat. Off. ............ 564/310
0053678 6/1982 European Pat. Off. .
3226496 3/1983 Fed. Rep. of Germany .
3603291 8/1987 Fed. Rep. of Germany .

OTHER PUBLICATIONS

Chemical Abstract, vol. 94, 102 795 (1981).
Zh. Org. Khim. 17, 268-272 [1981].
Chemical Abstract, vol. 94, 173 972 (1981).
Seikei Daigaku Kogakubu Hokoku 37, 2449 [1984].
Chemical Abstract, vol. 101, 171-178 (1984).
J. Heterocyclic Chem. 23, 1535-1538 (1986).
Chemistry Letters, 1982, pp. 543-546.
J. Heterocylc. Chem. 22, 565-568 [1985].
J. Am. Chem. Soc., 76, 300 [1954].

Primary Examiner—Mary C. Lee
Assistant Examiner—Kurt G. Briscoe
Attorney, Agent, or Firm—Sprung Horn Kramer & Woods

[57] ABSTRACT

Novel insecticidally active compounds of the formula

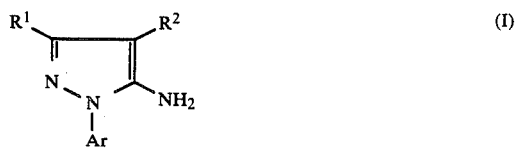

in which
$R^1$ represents halogenoalkyl,
$R^2$ represents cyano, hydroxycarbonyl, carbamoyl, thiocarbamoyl, alkoxycarbonyl, N-alkylcarbamoyl or N,N-dialkylcarbamoyl, or represents alkenyloxycarbonyl, N-alkenylcarbamoyl, N,N-dialkenylcarbamoyl, alkinyloxycarbonyl, N-alkinylcarbamoyl, N,N-dialkinylcarbamoyl or N-arylcarbamoyl and
Ar represents substituted phenyl, with the exception of the 4-nitrophenyl radical.

11 Claims, No Drawings

5-AMINO-3-HALOGENOALKYL-1-ARYL-PYRAZOLES, COMPOSITION CONTAINING THEM, AND METHOD OF USING THEM TO COMBAT INSECTS

The invention relates to new 5-amino-3-halogenoalkyl-1-aryl-pyrazoles, several processes for their preparation and their use as insecticides.

It is already known that certain 5-amino-1-aryl-pyrazoles, such as, for example, 4-cyano-5-propionamido-1-(2,4,6-trichlorophenyl)-pyrazole or 4-cyano-5-propionamido-1-(2,3,4-trichlorophenyl)-pyrazole, have a good herbicidal action (compare, for example, DE-OS (German Published Specification)No. 3,226,513).

Certain 5-amino-3-halogenoalkyl-1-aryl-pyrazoles, such as, for example, 5-amino-4-cyano-3-trifluoromethyl-1-phenyl-pyrazole, 5-amino-4-cyano-3-pentafluoroethyl-1-phenyl-pyrazole, 5-amino-4-cyano-3-heptafluoropropyl-1-phenyl-pyrazole, 5-amino-4-methoxycarbonyl-3-trifluoromethyl-1-phenyl-pyrazole, 5-amino-4-carbamoyl-3-trifluoromethyl-1-phenyl-pyrazole, 5-amino-4-cyano-3-trifluoromethyl-1-(4-nitrophenyl)-pyrazole, 5-amino-4-ethoxycarbonyl-3-trifluoromethyl-1-phenyl-pyrazole or 5-amino-4-methoxycarbonyl-3-trifluoromethyl-1-(4-nitrophenyl)-pyrazole, are furthermore known (compare Zh. org. Khim. 16, 1694–1698 [1980] or C.A.: 94: 102 795 w; Zh. org. Khim. 17, 268–272 [1981] or C.A.: 94: 17 39 714; Seikei Daigaku Kogakubu Hokoku 37, 2449–2450 [1984] or C.A.: 101: 171 178 x ; and J. Heterocyclic Chem. 23, 1535–1538 [1986]).

Nothing is as yet known of an insecticidal activity of these already known compounds.

New 5-amino-3-halogenoalkyl-1-aryl-pyrazoles of the general formula (I)

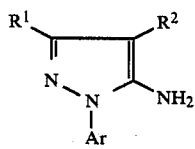

in which
R$^1$ represents halogenoalkyl,
R$^2$ represents cyano, hydroxycarbonyl, carbamoyl, thiocarbamoyl, alkoxycarbonyl, N-alkylcarbamoyl or N,N-dialkylcarbamoyl, or represents alkenyloxycarbonyl, N-alkenylcarbamoyl, N,N-dialkenylcarbamoyl, alkinyloxycarbonyl, N-alkinylcarbamoyl, N,N-dialkinylcarbamoyl or N-arylcarbamoyl and
Ar represents substituted phenyl, with the exception of the 4-nitrophenyl radical,
have been found.

It has furthermore been found that the new 5amino-3-halogenoalkyl-1-aryl-pyrazoles of the general formula (I)

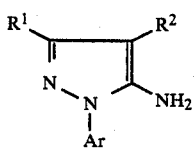

in which
R$^1$ represents halogenoalkyl,
R$^2$ represents cyano, hydroxycarbonyl, carbamoyl, thiocarbamoyl, alkoxycarbonyl, N-alkylcarbamoyl or N,N-dialkylcarbamoyl, or represents alkenyloxycarbonyl, N-alkenylcarbamoyl, N,N-dialkenylcarbamoyl, alkinyloxycarbonyl, N-alkinylcarbamoyl, N,N-dialkinylcarbamoyl or N-arylcarbamoyl and
Ar represents substituted phenyl, with the exception of the 4-nitrophenyl radical,
are obtained by a process in which
(a) to obtain compounds of the formula

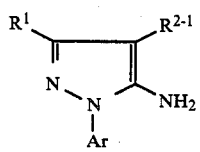

in which
R$^1$ and Ar have the abovementioned meaning and
R$^{2\text{-}1}$ represents cyano, carbamoyl, thiocarbamoyl, alkoxycarbonyl, N-alkylcarbamoyl, N,N-dialkylcarbamoyl, alkenyloxycarbonyl, N-alkenylcarbamoyl, N,N-dialkenylcarbamoyl, alkinyloxycarbonyl, N-alkinylcarbamoyl or N,N-dialkinylcarbamoyl, or represents N-arylcarbamoyl,
N-arylhydrazide halides of the formula (II)

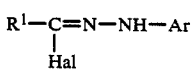

in which
R$^1$ and Ar have the abovementioned meaning and
Hal represents halogen,
are reacted with acetonitrile derivatives of the formula (III)

in which
R$^{2\text{-}1}$ has the abovementioned meaning, if appropriate in the presence of a diluent and if appropriate in the presence of an acid-binding agent, or by a process in which
(b) to obtain compounds of the abovementioned formula (Ia) in which R$^1$, R$^{2\text{-}1}$ and Ar have the abovementioned meaning, 2-chloro-acrylonitrile derivatives of the formula (IV)

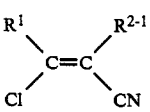

in which
R$^1$ and R$^{2\text{-}1}$ have the abovementioned meaning, are reacted with arylhydrazines of the formula (V)

in which
Ar has the abovementioned meaning, if appropriate in the presence of a diluent and if appropriate in the presence of an acid-binding agent, or by a process in which (c) to obtain compounds of the formula

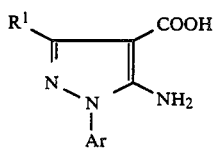

in which

R¹ and Ar have the abovementioned meaning, the 5-amino-3-halogenoalkyl-1-aryl-pyrazoles obtainable with the aid of processes (a) or (b), of the formula (Ic)

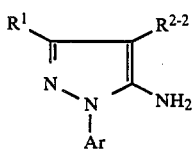

in which

R¹ and Ar have the abovementioned meaning and
R$^{2-2}$ represents alkoxycarbonyl, alkenyloxycarbonyl or alkinyloxycarbonyl, are hydolyzed with acids, if appropriate in the presence of a diluent.

Finally, it has been found that the new 5-amino-3-halogenoalkyl-1-aryl-pyrazoles of the formula (I) have an insecticidal action.

Surprisingly, the 5-amino-3-halogenoalkyl-1-aryl-pyrazoles of the general formula (I) according to the invention exhibit a better insecticidal activity than the 5-amino-1-aryl-pyrazoles known from the prior art, such as, for example, 4-cyano-5-propionamido-1-(2,4,6-trichlorophenyl)-pyrazole or 4-cyano-5-propionamido-1-trichlorophenyl)-pyrazole, which are closely related compounds chemically.

Formula (I) provides a general definition of the 5-amino-3-halogenoalkyl-1-aryl-pyrazoles according to the invention. Preferred compounds of the formula (I) are those in which R¹ represents straight-chain or branched halogenoalkyl with 1 to 4 carbon atoms and 1 to 9 identical or different halogen atoms, R² represents cyano, or represents hydroxycarbonyl, or represents carbamoyl or thiocarbamoyl, or represents in each case straight-chain or branched alkoxycarbonyl, N-alkylcarbamoyl or N,N-dialkylcarbamoyl with in each case 1 to 4 carbon atoms in the individual alkyl parts, or represents in each case straight-chain or branched alkenyloxycarbonyl, N-alkenylcarbamoyl or N,N-dialkenylcarbamoyl with in each case 3 to 6 carbon atoms in the individual alkenyl parts, or represents in each case straight-chain or branched alkinyloxycarbonyl, N-alkinylcarbamoyl or N,N-dialkinylcarbamoyl with in each case 3 to 6 carbon atoms in the individual alkinyl parts, or represents N-phenylcarbamoyl, and Ar represents phenyl which is monosubstituted or polysubstituted by identical or different substituents, with the exception of the 4-nitrophenyl radical, possible substituents being: halogen, cyano, nitro and in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl and alkoxycarbonyl with in each case 1 to 4 carbon atoms in the individual alkyl parts and, where appropriate, 1 to 9 identical or different halogen atoms.

Particularly preferred compounds of the formula (I) are those in which

R¹ represents trifluoromethyl, dichlorofluoromethyl, difluorochloromethyl, difluoromethyl, trifluoroethyl, trifluorochloroethyl, trifluorodichloroethyl, difluorodichloroethyl, tetrafluoroethyl, pentafluoroethyl, heptafluoropropyl or nonafluorobutyl, R² represents cyano, or represents hydroxycarbonyl, or represents carbamoyl or thiocarbamoyl, or represents methoxycarbonyl, ethoxycarbonyl, N-methylcarbamoyl, N,N-dimethylcarbamoyl, N-ethylcarbamoyl or N,N-diethylcarbamoyl and Ar represents phenyl which is substituted by one to five identical or different substituents, with the exception of the 4-nitrophenyl radical, possible substituents being: fluorine, chlorine, bromine, iodine, cyano, nitro, methyl, ethyl, n- or i-propyl, n-, i-, s- or t-butyl, methoxy, ethoxy, methylthio, methylsulphinyl, methylsulphonyl, methoxycarbonyl, ethoxycarbonyl, trifluoromethyl, dichlorofluoromethyl, difluorochloromethyl, difluoromethyl, pentafluoroethyl, tetrafluoroethyl, trifluorochloroethyl, trifluoroethyl, difluorochloroethyl, trifluorodichloroethyl and a radical —X—R³, wherein X represents oxygen, sulphur, sulphinyl or sulphonyl and R³ represents trifluoromethyl, dichlorofluoromethyl, difluorochloromethyl, difluoromethyl, pentafluoroethyl, tetrafluoroethyl, trifluorochloroethyl, trifluoroethyl, difluorochloroethyl or trifluorodichloroethyl.

The following 5-amino-3-halogenoalkyl-1-aryl-pyrazoles of the general formual (I) may be mentioned specifically, in addition to the compounds mentioned in the preparation examples:

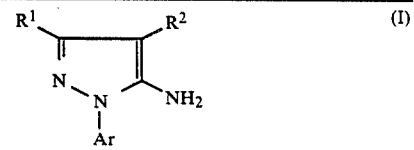

| R¹ | R² | Ar |
|----|----|-----|
| CF₃ | CN | 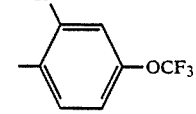 |
| CF₃ | CN | 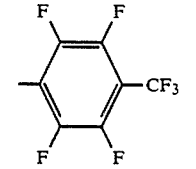 |

-continued $$\underset{Ar}{\underset{|}{N}}\overset{R^1}{\underset{N}{\overset{}{\bigtriangleup}}}\overset{R^2}{\underset{NH_2}{}}\quad (I)$$

| R¹ | R² | Ar |
|---|---|---|
| CF₃ | CONH₂ | 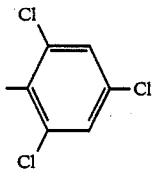 |
| CF₃ | CSNH₂ | 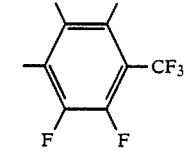 |
| CF₃ | CONH₂ | 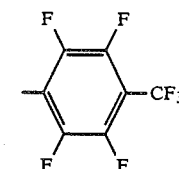 |
| CF₃ | CSNH₃ | 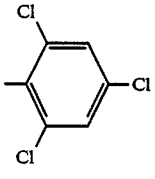 |
| CF₃ | CONH₂ | 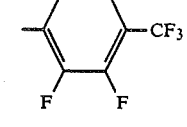 |
| CF₃ | CSNH₂ | 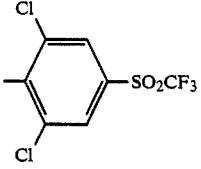 |
| CF₃ | CONH₂ | 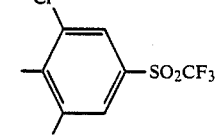 |
| CF₃ | CSNH₂ | 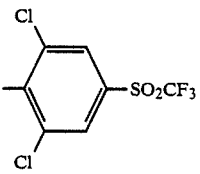 |

-continued $$\underset{Ar}{\underset{|}{N}}\overset{R^1}{\underset{N}{\overset{}{\bigtriangleup}}}\overset{R^2}{\underset{NH_2}{}}\quad (I)$$

| R¹ | R² | Ar |
|---|---|---|
| CF₃ | CONH₂ | 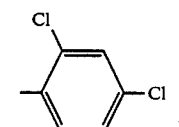 |
| CF₃ | CSNH₂ | 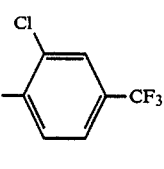 |
| CF₃ | COOC₂H₅ | 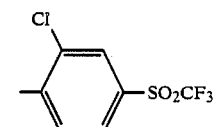 |
| CF₃ | COOH | 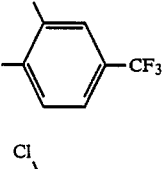 |
| CF₃ | COOH | 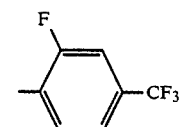 |
| CF₃ | COOH | 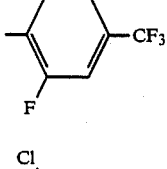 |
| CF₃ | COOC₂H₅ | 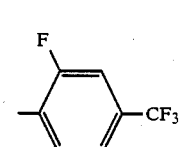 |
| CF₃ | COOH | 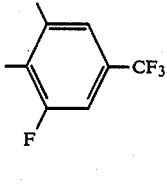 |

-continued

Formula (I): pyrazole with $R^1$ at 3-position, $R^2$ at 4-position, $NH_2$ at 5-position, and Ar on N1.

| $R^1$ | $R^2$ | Ar |
|---|---|---|
| $CF_3$ | $COOC_2H_5$ | 2,3,5,6-tetrafluoro-4-(trifluoromethyl)phenyl |
| $C_2F_5$ | $CN$ | 2,6-dichloro-4-(trifluoromethyl)phenyl |
| $C_2F_5$ | $CONH_2$ | 2,6-dichloro-4-(trifluoromethyl)phenyl |
| $C_2F_5$ | $CSNH_2$ | 2,6-dichloro-4-(trifluoromethyl)phenyl |
| $C_2F_5$ | $COOC_2H_5$ | 2,6-dichloro-4-(trifluoromethyl)phenyl |
| $C_2F_5$ | $COOH$ | 2,6-dichloro-4-(trifluoromethyl)phenyl |
| $C_3F_7$ | $CN$ | 2,6-dichloro-4-(trifluoromethyl)phenyl |
| $C_3F_7$ | $CONH_2$ | 2,6-dichloro-4-(trifluoromethyl)phenyl |
| $C_3F_7$ | $CSNH_2$ | 2,6-dichloro-4-(trifluoromethyl)phenyl |
| $C_3F_7$ | $COOC_2H_5$ | 2,6-dichloro-4-(trifluoromethyl)phenyl |
| $C_3F_7$ | $COOH$ | 2,6-dichloro-4-(trifluoromethyl)phenyl |
| $CCl_2F$ | $CN$ | 2,6-dichloro-4-(trifluoromethyl)phenyl |
| $CCl_2F$ | $CONH_2$ | 2,6-dichloro-4-(trifluoromethyl)phenyl |
| $CCl_2F$ | $CSNH_2$ | 2,6-dichloro-4-(trifluoromethyl)phenyl |
| $CCl_2F$ | $COOC_2H_5$ | 2,6-dichloro-4-(trifluoromethyl)phenyl |
| $CCl_2F$ | $COOH$ | 2,6-dichloro-4-(trifluoromethyl)phenyl |

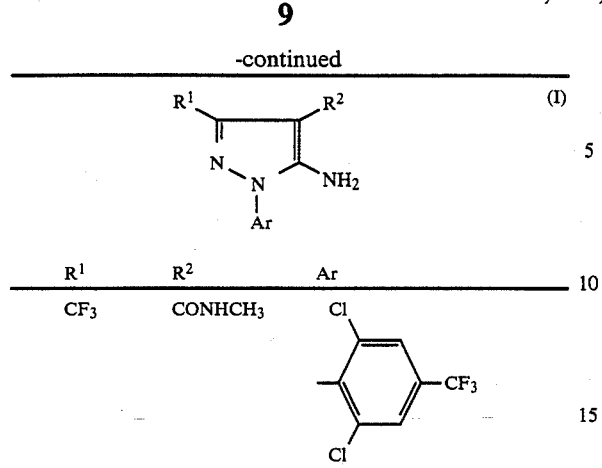

| R¹ | R² | Ar |
|---|---|---|
| CF₃ | CONHCH₃ | (2,6-dichloro-4-trifluoromethylphenyl) |

If, for example, N-(2,2,2-trifluoro-1-bromoethylidene)-N'-(2,6-dichloro-4-trifluoromethylphenyl)-hydrazine and malodinitrile are used as starting substances, the course of the reaction in process (a) according to the invention can be represented by the following equation:

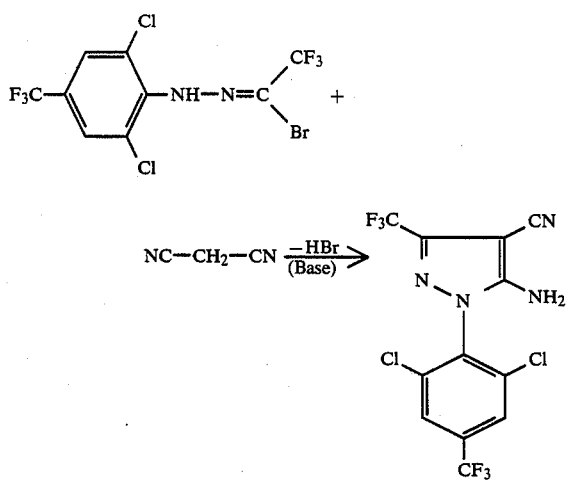

If, for example, (2,2,2-trifluoro-1-chloroethylidene)-malodinitrile and 2,6-dichloro-4-trifluoromethoxyphenylhydrazine are used as starting substances, the course of the reaction in process (b) according to the invention can be represented by the following equation:

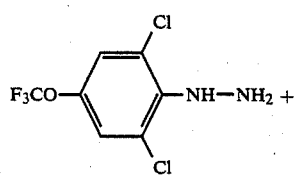

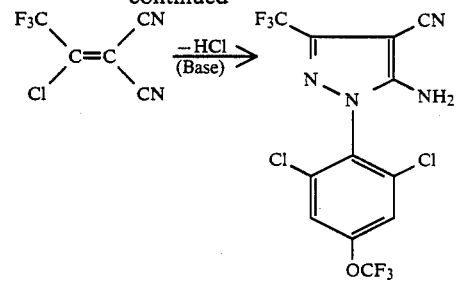

If, for example, 5-amino-4-ethoxycarbonyl-3-trifluoromethyl-1-(2,4,6-trichlorophenyl)-pyrazole is used as the starting compound, the course of the reaction in process (c) according to the invention can be represented by the following equation:

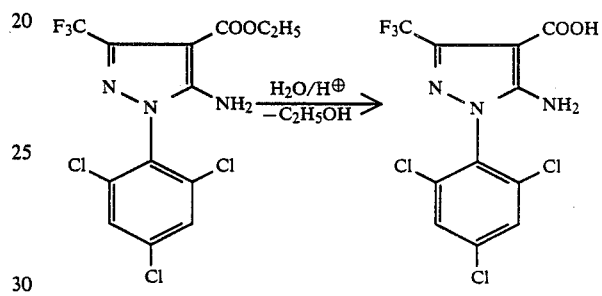

Formula (II) provides a general definition of the N-arylhydrazide halides required as starting substances for carrying out process (a) according to the invention. In this formula (II), R¹ and Ar preferably represent those radicals which have already been mentioned as preferred for these substituents in connection with the description of the substances of the formula (I) according to the invention.

Hal preferably represents chlorine or bromine.

The N-arylhydrazide halides of the formula (II) are known in some cases (compare, for example, Chem. Lett. 1982, 543; J. Heterocycl. Chem. 22, 565 [1985]; and European Pat. No. 1,019).

They are obtained, for example, by a process in which arylhydrazines of the formula (V)

Ar—NH—NH₂       (V)

in which

Ar has the abovementioned meaning, are initially reacted in a first stage with aldehydes of the formula (VI)

  (VI)

in which

R¹ has the abovementioned meaning, or with hydrates or hemiacetals thereof, of the formula (VII)

  (VII)

in which $R^1$ has the abovementioned meaning and
$R^4$ represents hydrogen or alkyl, if appropriate in the presence of a diluent, such as, for example, ethanol or toluene, and if appropriate in the presence of a reaction auxiliary, such as, for example, sulphuric acid, at temperatures between −30 C. and +150 C., and the arylhydrazones thus obtainable, of the formula (VIII)

     (VIII)

in which $R^1$ and Ar have the abovementioned meaning, are reacted in a 2nd stage with halogenating agents, such as, for example, N-bromosuccinimide, N-chlorosuccinimide or bromine, if appropriate in the presence of a diluent, such as, for example, dimethylformamide or acetic acid, at temperatures between −30° C. and +100° C.

The aldehydes of the formula (VI) and hydrates or hemiacetals thereof of the formula (VII) are generally known compounds of organic chemistry (compare, for example, J. Am. chem. Soc., 76, 300 [1954]).

Formula (III) provides a general definition of the acetonitrile derivatives furthermore required as starting substances for carrying out process (a) according to the invention. In this formula (III), $R^{2-1}$ preferably represents those radicals which have already been mentioned as preferred for the substituent $R^2$ in connection with the description of the substances of the formula (I) according to the invention, with the exception of the hydroxycarbonyl radical.

The acetonitrile derivatives of the formula (III) are generally known compounds of organic chemistry.

Formula (IV) provides a general definition of the 2-chloroacrylonitrile derivatives required as starting substances for carrying out process (b) according to the invention. In this formula (IV), $R^1$ preferably represents those radicals which have already been mentioned as preferred for these substituents in connection with the description of the substances of the formula (I) according to the invention. $R^{2-1}$ preferably represents those radicals which have already been mentioned as preferred for the substituent $R^2$ in connection with the description of the substances of the formula (I) according to the invention, with the exception of the hydroxycarbonyl radical.

The 2-chloroacrylonitrile derivatives of the formula (IV) are known or are obtainable by processes analogous to known processes (compare, for example, Zh. org. Khim. 16, 1694 [1980] or C.A.: 94: 102 795 w and Zh. org. Khim. 17, 268 [1981] or C.A.: 94: 174 971 y).

Formula (V) provides a general definition of the arylhydrazines furthermore required as starting substances for carrying out process (b) according to the invention and for the synthesis of the precursors of the formula (II). In this formula (V), Ar preferably represents those radicals which have already been mentioned as preferred for these substituents in connection with the description of the substances of the formula (I) according to the invention.

The arylhydrazines of the formula (V) are known (compare, for example, European Pat. No.154,115, European Pat. No. 187,285 and European Pat. No. 34,945), or they are obtainable by generally known processes analogously to known compounds (compare, for example, Houben-Weyl, "Methoden der organischen Chemie" ("Methods of Organic Chemistry"), Volume X, 2, Thieme Verlag, Stuttgart 1967).

Formula (Ia) provides a general definition of the 5-amino-3-halogenoalkyl-1-aryl-pyrazoles required as starting substances for carrying out process (c) according to the invention. In this formula (Ia), $R^1$ and Ar preferably represent those radicals which have already been mentioned as preferred for these substituents in connection with the description of the substances of the formula (I) according to the invention.

$R^{2-2}$ preferably represents straight-chain or branched alkoxycarbonyl with 1 to 4 carbon atoms, in particular ethoxycarbonyl. The 5-amino-3-halogenoalkyl-1-aryl-pyrazoles of the formula (Ia) are compounds according to the invention and are obtainable with the aid of processes (a) or (b) according to the invention.

Possible diluents for carrying out process (a) according to the invention are inert organic solvents. Solvents which are preferably used are polar solvents, such as, for example, dioxane, tetrahydrofuran, dimethylformamide, ethanol, methanol, t-butanol or ethylene glycol monomethyl ether.

Process (a) according to the invention is preferably carried out in the presence of a suitable acid-binding agent. Possible acid-binding agents are all the inorganic or organic bases which can usually be employed. Bases which are preferably used are alkali metal hydrides, hydroxides or alcoholates, such as, for example, sodium hydride, sodium hydroxide, sodium methylate, sodium ethylate, sodium isopropylate, potassium isopropylate or potassium t-butylate.

The reaction temperatures can be varied within a substantial range in carrying out process (a) according to the invention. The reaction is in general carried out at temperatures between −30° C. and +150° C., preferably at temperatures between 0° C. and +100° C.

For carrying out process (a) according to the invention, in general 1.0 to 10.0 mols, preferably 1.0 to 2.0 mols of acetonitrile derivative of the formula (III) and if appropriate 1.0 to 10.0 mols, preferably 1.0 to 2.0 mols, of acid-binding agent are employed per mol of N-arylhydrazide halide of the formula (II). The reaction is carried out and the reaction products are worked up and isolated by generally known processes (compare also the preparation examples).

Possible diluents for carrying out process (b) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylpyrrolidone or hexamethylphosphoric acid triamide, or esters, such as ethyl acetate.

Process (b) according to the invention is preferably carried out in the presence of a suitable acid-binding agent. Possible acid-binding agents are all the customary inorganic or organic bases. Bases which are preferably used are teriiary amines, such as triethylamine, N,N-dimethylaniline, pyridine, diazabicyclooctane (DABCO), diazabicyclononene (DBN) or diazabicycloundecene (DBU).

It is also possible for the arylhydrazine of the formula (V) used as the reaction partner to be employed simultaneously as the acid-binding agent in an appropriate excess.

The reaction temperatures can be varied within a substantial range in carrying out process (b) according to the invention. The reaction is in general carried out at temperatures between −30° C. and +150° C., preferably at temperatures between 0° C. and +100° C.

For carrying out process (b) according to the invention, in general 1.0 to 20.0 mols preferably 1.0 to 5.0 mols of arylhydrazine of the formula (V) and if appropriate 1.0 to 20.0 mols preferably 1.0 to 2.0 mols of acid-binding agent are employed per mol of 2-chloroacrylonitrile derivative of the formula (IV). The reaction is carried out and the reaction products are worked up and isolated by generally known processes (compare also the preparation examples).

Process (c) according to the invention is carried out in the presence of a suitable acid. Possible acids are all the inorganic or organic acids which can usually be employed. Acids which are preferably used are sulphuric acid, hydrochloric acid or p-toluenesulphonic acid.

Possible diluents for carrying out process (c) according to the invention are polar inorganic or organic solvents or mixtures thereof with water. The sulphuric acid simultaneously employed as the reagent is preferably used as the diluent in an appropriate excess.

The reaction temperatures can be varied within a substantial range in carrying out process (c) according to the invention. The reaction is in general carried out at temperatures between 0° C. and +150° C., preferably at temperatures between +20° C. and +100° C.

For carrying out process (c) according to the invention, in general 1.0 to 30 mols preferably 1.0 to 10.0 mols of aqueous acid are employed per mol of 5-amino-3-halogenoalkyl-1-aryl-pyrazole of the formula (Ia). The reaction is carried out and the reaction products are worked up and isolated by generally known processes (compare also the preparation examples).

The active compounds are suitable for combating animal pests, preferably anthropods and in particular insects, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. Bucculatrix thurberiella, Phyllocnistis citrella, Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphiaallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.

The active compounds according to the invention can thereby be use with particularly good success for combating leaf and soil insects, such as, for example, against the larvae of the horseradish leaf beetle (*Phaedon cochleariae*).

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

PREPARATION EXAMPLES

Example 1

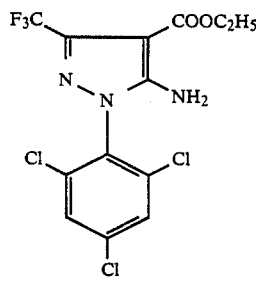

(Process a)

2.3 g (0.02 mol) of ethyl cyanoacetate are added dropwise to a solution of 1.36 g (0.02 mol) of sodium ethanolate in 20 ml of ethanol and the mixture is heated at the reflux temperature for 15 minutes. 7.4 g (0.02 mol) of N-(2,4,6-trichlorophenyl)-trifluoroacetohydrazide bromide are then added dropwise and the mixture is boiled at the reflux temperature for a further 5 hours. After cooling to room temperature, the sodium bromide is filtered off and the filtrate is concentrated. Separation of the residue by column chromatography gives 4.73 g (59% of theory) of 5-amino-4-ethoxycarbonyl-3-trifluoromethyl-1-(2,4,6-trichlorophenyl)-pyrazole of melting point 114°–116° C.

EXAMPLE 2

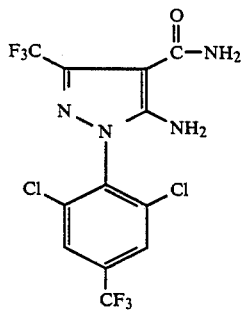

(Process a)

4.20 g (0.05 mol) of cyanoacetamide are added to a solution of 3.40 g (0.05 mol) of sodium ethanolate in 20 ml of ethanol and the mixture is subsequently stirred at 2520 C. for 45 minutes. After dropwise addition of 20.2 g (0.05 mol) of N-(2,6-dichloro-4-trifluoromethyl-phenyl)-trifluoroacetohydrazide bromide, with cooling, the mixture is subsequently stirred at 0° C. for 1 hour. Removal of the sodium bromide by filtration, concentration and purification by column chromatography gives 1.23 g (6% of theory) of 5-amino-4-aminocarbonyl-3-trifluoromethyl-1-(2,6-dichloro-4-trifluoro of melting point 167°–169° C.

EXAMPLE 3

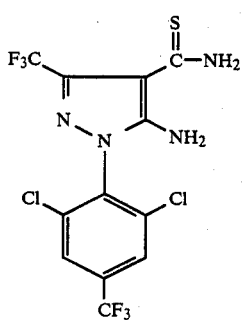

(Process a)

From the reaction of 3.40 g (0.05 mol) of sodium ethanolate, 5.00 g (0.05 mol) of cyanothioacetamide and 20.2 g (0.05 mol) of N-(2,6-dichloro-4-trifluoromethyl-phenyl)-trifluoroacetohydrazide bromide in 20 ml of ethanol by the abovementioned process, 2.50 g (12% of theory) of 5-amino-4-aminothiocarbonyl-3-trifluoromethyl-1-(2,6-dichloro-4-trfluoromethylphenyl)-pyrazole of melting point 123° C.–125° C. are isolated after column chromatography.

EXAMPLE 4

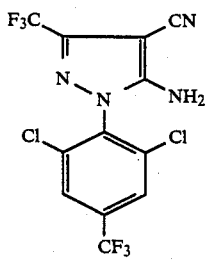

(Process b)

A mixture of 2.45 g (0.01 mol) of 2,6-dichloro-4-trifluoromethyl-phenylhydrazine and 1.01 g (0.01 mol) of triethylamine in 5 ml of methylene chloride is added dropwise to a solution of 1.81 g (0.01 mol) of (2,2,2-trifluoro-1-chloro-ethylidene)malodinitrile in 20 ml of methylene chloride. After the mixture has been stirred at room temperature for 7 hours, it is concentrated and the residue is separated by column chromatography. 2.60 g (67% of theory) of 5-amino-4-cyano-3-trifluoromethyl-1-(2,6-dichloro-4-trifluoromethylphenyl)-pyrazole of melting point 196° C.–200° C. are isolated.

EXAMPLE 5

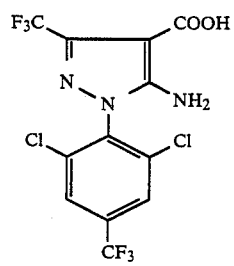

(Process c)

3.05 G (0.007 mol) of 5-amino-4-ethoxycarbonyl-3-trifluoromethyl-1-(2,6-dichloro-4-trifluoromethyl-phenyl)pyrazole in 14 ml of concentrated sulphuric acid are heated at 75° C. for 5 hours. After the mixture has been cooled to room temperature, it is diluted with ice-water and filtered with suction. 2.45 g (86% of theory) of 5-amino-4-hydroxycarbonyl-3-trifluoromethyl-1-(2,6-dichloro-4-trifluoromethylphenyl)pyrazole of melting point 191° C.–195° C. (decomposition) are obtained.

The following 5-amino-3-halogenoalkyl-1-aryl-pyrazoles of the general formula (I) are obtained in a corresponding manner in accordance with the general statements on the preparation:

$$\begin{array}{c} R^1 \quad\quad R^2 \\ \diagdown \diagup \\ N \\ | \\ Ar \end{array} \quad NH_2 \quad (I)$$

| Example No. | $R^1$ | $R^2$ | Ar | Melting Point/°C. |
|---|---|---|---|---|
| 6 | $CF_3$ | CN | 2,4,6-trichlorophenyl | 168–171 |
| 7 | $CF_3$ | CN | 2-chloro-4-trifluoromethylphenyl | 131–133 |
| 8 | $CF_3$ | CN | 2,4,6-trichloro-3-trifluoromethylphenyl | 185–191 |
| 9 | $CF_3$ | CN | 2,6-dichloro-4-trifluoromethylsulphonylphenyl | 196–198 |

-continued $$R^1, R^2, Ar\text{-substituted pyrazole} \quad (I)$$

(structure: pyrazole with R¹ at 3-position, R² at 4-position, NH₂ at 5-position, Ar on N1)

| Example No. | R¹ | R² | Ar | Melting Point/°C |
|---|---|---|---|---|
| 10 | CF₃ | COOC₂H₅ | 2,6-dichloro-4-trifluoromethylphenyl | 126–127 |

PREPARATION OF THE STARTING COMPOUNDS

EXAMPLE II-1

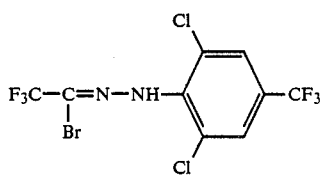

4.45 g (0.025 mol) of N-bromosuccinimide are added in portions to a solution of 8.12 g (0.025 mol) of trifluoroacetaldehyde N-(2,6-dichloro-4-trifluoromethylphenyl)-hydrazone in 14 ml of dimethylformamide at room temperature, whereupon an exothermic reaction occurs. The mixture is stirred at room temperature for 3 hours, the dimethylformamide is distilled off and 20 ml of petroleum ether are added to the residue. After the succinimide which has precipitated has been filtered off with suction, the filtrate is concentrated and the residue is subjected to bulb tube distillation. 9.26 g (91.7% of theory) of N-(2,6-dichloro-4-trifluoromethylphenyl)-trifluoroacetohydrazide bromide of boiling point 110° C. under 0.06 mbar and of refractive index $n_D^{20}$ 1.510 are obtained.

EXAMPLE II-2

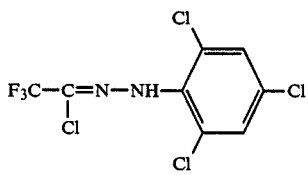

3.2 g (0.011 mol) of trifluoroacetaldehyde N-(2,4,6-trichlorophenyl)-hydrazone and 1.5 g (0.011 mol) of N-chlorosuccinimide in 3.3 ml of dimethylformamide are stirred at room temperature for 3 hours. After the mixture has been concentrated, petroleum ether is added to the residue, the mixture is filtered and the filtrate is concentrated again. Bulb tube distillation of the residue at 150° C. (0.5 mbar) gives 3.28 g (89.6% of theory) of N-(2,4,6-trichlorophenyl)-trifluoroacetohydrazide chloride of refractive index $n_D^{20}$ 1.549.

The following N-arylhydrazide halides of the general formula (II) are obtained in a corresponding manner and in accordance with the general statements on the preparation:

$$R^1-\underset{Hal}{C}=N-NH-Ar \quad (II)$$

| Example No. | R¹ | Hal | Ar | Physical properties |
|---|---|---|---|---|
| II-3 | CF₃ | Br | 2,4-dichlorophenyl | boiling point 125° C./0.08 mbar |
| II-4 | CF₃ | Cl | 2,6-dichloro-4-trifluoromethylphenyl | boiling point 130° C./0.5 mbar |
| II-5 | CF₃ | Br | 2,3-dichloro-4-trifluoromethyl-6-chlorophenyl | melting point 62–63° C. |
| II-6 | CF₃ | Br | 2-chloro-4-trifluoromethylphenyl | boiling point 95° C./0.05 mbar |
| II-7 | CF₃ | Cl | 2-chloro-4-trifluoromethylphenyl | boiling point 90° C./0.13 mbar |
| II-8 | CF₃ | Br | 2,6-dichloro-4-trifluoromethylsulfonylphenyl | melting point 48–50° C. |

EXAMPLE VIII-1

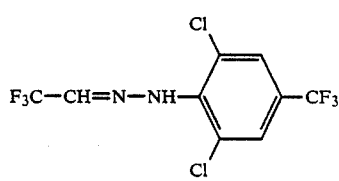

A mixture of 100 g (0.69 mol) of trifluoroacetaldehyde ethyl-hemiacetal and 169.1 g (0.69 mol) of 2,6-dichloro-4-trifluoromethylphenyl hydrazine is heated at 100° C. for 6 hours. After the volatile components have been removed, the residue is recrystallized from petroleum ether. 200 g (89%) of trifluoroacetaldehyde N-

(2,6-dichloro-4-trifluoromethylphenyl)-hydrazone of melting point 45° C. to 46° C. are isolated.

The following aldehyde N-arylhydrazones of the general formula (VIII) are obtained in a corresponding manner and in accordance with the general statements on the preparation:

$$R^1-CH=N-NH-Ar \quad (VIII)$$

| Example No. | $R^1$ | Ar | Melting point/°C. |
|---|---|---|---|
| VIII-2 | $CF_3$ | (2,4-dichlorophenyl) | 43–45 |
| VIII-3 | $CF_3$ | (2,6-dichloro-4-trifluoromethylphenyl) | 50–52 |
| VIII-4 | $CF_3$ | (3-chloro-4-trifluoromethylphenyl) | 63–65 |
| VIII-5 | $CF_3$ | (2,6-dichloro-4-trifluoromethylsulfonylphenyl) | 124–126 |

Use Examples

The compounds shown below were employed as comparison substances (prior art) in the use examples which follow:

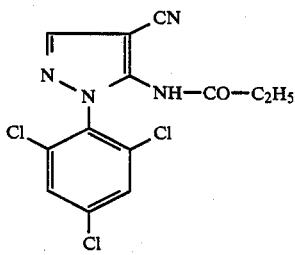

4-Cyano-5-propionamido-1-(2,4,6-trichlorophenyl)-pyrazole

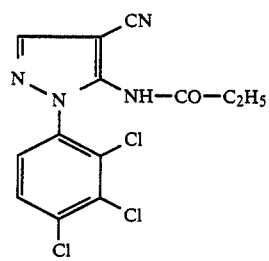

4-Cyano-5-propionamido-1-(2,3,4-trichlorophenyl)-pyrazole (both known from DE-OS No. (German Published Specification) 3,226,513)

EXAMPLE A

Phaedon larvae test
Solvent: 7 parts by weight
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test for example, the following compounds from the preparation examples show a superior activity compared with the prior art: 2, 4, 6, 7, 9, 10.

It will be understood that the specification and examples are illustrative but not limitative of the present invention and that other embodiments within the spirit and scope of the invention will suggest themselves to those skilled in the art.

We claim:

1. A 5-amino-3-halogenoalkyl-1-aryl-pyrazole of the formula

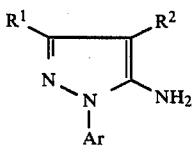

in which
$R^1$ represents halogenoalkyl,
$R^2$ represents cyano, hydroxycarbonyl, carbamoyl, thiocarbamoyl, alkoxycarbonyl, N-alkylcarbamoyl or N,N-dialkylcarbamoyl, or represents alkenyloxycarbonyl, N-alkenylcarbamoyl, N,N-dialkenylcarbamoyl, alkinyloxycarbonyl, N-alkinylcarbamoyl, N,N-dialkinylcarbamoyl or N-arylcarbamoyl and Ar represents substituted phenyl, with the exception of the 4-nitrophenyl radical.

2. A 5-amino-3-halogenoalkyl-1-aryl-pyrazole according to claim 1, in which

R¹ represents straight-chain or branched halogenoalkyl with 1 to 4 carbon atoms and 1 to 9 identical or different halogen atoms, R² represents cyano, or represents hydroxycarbonyl, or represents carbamoyl or thiocarbamoyl, or represents in each case straight-chain or branched alkoxycarbonyl, N-alkylcarbamoyl or N,N-dialkylcarbamoyl with in each case 1 to 4 carbon atoms in the individual alkyl parts, or represents in each case straight-chain or branched alkenyloxycarbonyl, N-alkenylcarbamoyl or N,N-dialkenylcarbamoyl with in each case 3 to 6 carbon atoms in the individual alkenyl parts, or represents in each case straight-chain or branched alkinyloxycarbonyl, N-alkinylcarbamoyl or N,N-dialkinylcarbamoyl with in each case 3 to 6 carbon atoms in the individual alkinyl parts, or represents N-phenylcarbamoyl, and Ar represents phenyl which is monosubstituted or polysubstituted by identical or different substituents, with the exception of the 4-nitrophenyl radical, the substituents being halogen, cyano, nitro and in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl and alkoxycarbonyl with in each case 1 to 4 carbon atoms in the individual alkyl parts and, where appropriate, 1 to 9 identical or different halogen atoms.

3. A 5-amino-3-halogenoalkyl-1-aryl-pyrazole according to claim 1, in which

R¹ represents trifluoromethyl, dichlorofluoromethyl, difluorochloromethyl, difluoromethyl, trifluoroethyl, trifluorochloroethyl, trifluorodichloroethyl, difluorodichloroethyl, tetrafluoroethyl, pentafluoroethyl, heptafluoropropyl or nonafluorobutyl, R² represents cyano, or represents hydroxycarbonyl, or represents carbamoyl or thiocarbamoyl, or represents methoxycarbonyl, ethoxycarbonyl, N-methylcarbamoyl, N,N-dimethylcarbamoyl, N-ethylcarbamoyl or N,N-diethylcarbamoyl and Ar represents phenyl which is substituted by one to five identical or different substituents, with the exception of the 4-nitrophenyl radical, the substituents being fluorine, chlorine, bromine, iodine, cyano, nitro, methyl, ethyl, n- or i-propyl, n-, i-, s- or t-butyl, methoxy, ethoxy, methylthio, methylsulphinyl, methylsulphonyl, methoxycarbonyl, ethoxycarbonyl, trifluoromethyl, dichlorofluoromethyl, difluorochloromethyl, difluoromethyl, pentafluoroethyl, tetrafluoroethyl, trifluorochloroethyl, trifluoroethyl, difluorochloroethyl, trifluorodichloroethyl and a radical —X—R³, wherein X represents oxygen, sulphur, sulphinyl or sulphonyl and R³ represents trifluoromethyl, dichlorofluoromethyl, difluorochloromethyl, difluoromethyl, pentafluoroethyl, tetrafluoroethyl, trifluorochloroethyl, trifluoroethyl, difluorochloroethyl or trifluorodichloroethyl.

4. A compound according to claim 1, wherein such compound is 5-amino-4-aminocarbonyl-3-trifluoromethyl-1-(2,6-dichloro-4-trifluoromethylphenyl)-pyrazole of the formula

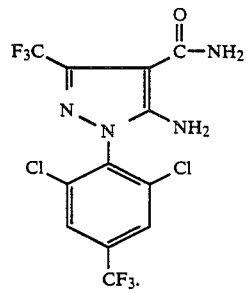

5. A compound according to claim 1, wherein such compound is 5-amino-4-cyano-3-trifluoromethyl-1-(2,6-dichloro-4-trifluoromrthylphenyl)-pyrazole of the formula

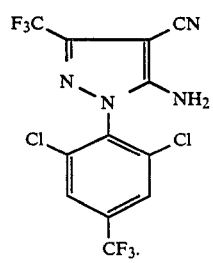

6. A compound according to claim 1, wherein such compound is 5-amino-4-cyano-3-trifluoromethyl-1-(2,4,6-trichlorophenyl)-pyrazole of the formula

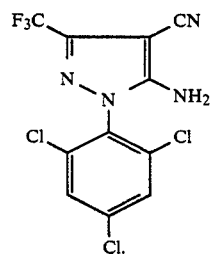

7. A compound according to claim 1, wherein such compound is 5-amino-4-cyano-3-trifluoromethyl-1-(2-chloro-4-trifluoromethylphenyl)-pyrazole of the formula

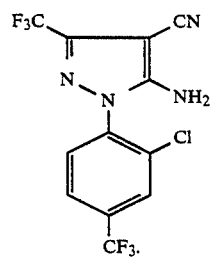

8. A compound according to claim 1, wherein such compound is 5-amino-4-cyano-3-trifluoromethyl-1-(2,6-dichloro-4-trifluromethylsulphonylphenyl)-pyrazole of the formula

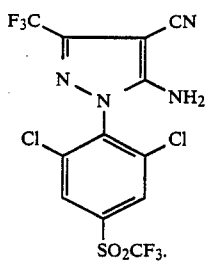

9. An insecticidal composition comprising an insecticidally effective amount of a compound according to claim 1 and a diluent.

10. A method of combating insects which comprises applying to such insects or to an insect habitat an insecticidally effective amount of a compound according to claim 1.

11. The method according to claim 10 wherein such compound is
5-amino-4-aminocarbonyl-3-trifluoromethyl-1-(2,6-dichloro-4-trifluoromethylphenyl)-pyrazole,
5-amino-4-cyano-3-trifluoromethyl-1-(2,6-dichloro-4-trifluoromethylphenyl)-pyrazole,
5-amino-4-cyano-3-trifluoromethyl-1-(2,4,6-trichlorophenyl)-pyrazole,
5-amino-4-cyano-3-trifluoromethyl-1-(2-chloro-4-trifluoromethylphenyl)-pyrazole or
5-amino-4-cyano-3-trifluoromethyl-1-(2,6-dichloro-4-trifluoromethylsulphonylphenyl)-pyrazole.

* * * * *